US009243353B2

United States Patent
Shirokaze et al.

(10) Patent No.: US 9,243,353 B2
(45) Date of Patent: Jan. 26, 2016

(54) STENT GRAFTS

(75) Inventors: Junichi Shirokaze, Tokyo (JP); Yasuharu Noishiki, Yokohama (JP)

(73) Assignees: ASAHI KASEI FIBERS CORP., Osaka (JP); NOI LAB INC., Kanagawa (JP)

( * ) Notice: Subject to any disclaimer, the term of this patent is extended or adjusted under 35 U.S.C. 154(b) by 0 days.

(21) Appl. No.: 13/357,150

(22) Filed: Jan. 24, 2012

(65) Prior Publication Data
US 2012/0226344 A1    Sep. 6, 2012

Related U.S. Application Data

(60) Provisional application No. 61/436,264, filed on Jan. 26, 2011.

(51) Int. Cl.
| *A61F 2/07* | (2013.01) |
| *D02G 1/02* | (2006.01) |
| *D03D 15/00* | (2006.01) |
| *A61L 31/14* | (2006.01) |
| *A61L 27/00* | (2006.01) |
| *D03D 3/02* | (2006.01) |

(52) U.S. Cl.
CPC ............ *D02G 1/0206* (2013.01); *A61L 31/146* (2013.01); *D03D 15/0061* (2013.01); *A61F 2/07* (2013.01); *A61L 27/00* (2013.01); *D03D 3/02* (2013.01); *D10B 2401/10* (2013.01); *D10B 2509/06* (2013.01)

(58) Field of Classification Search
None
See application file for complete search history.

(56) References Cited

U.S. PATENT DOCUMENTS

| 5,957,974 | A | * | 9/1999 | Thompson et al. .......... 623/1.13 |
| 6,352,561 | B1 |  | 3/2002 | Leopold et al. |
| 6,613,072 | B2 |  | 9/2003 | Lau et al. |
| 2006/0009835 | A1 |  | 1/2006 | Osborne et al. |
| 2006/0073467 | A1 |  | 4/2006 | Kuno et al. |
| 2006/0257456 | A1 |  | 11/2006 | Iwamoto et al. |

(Continued)

FOREIGN PATENT DOCUMENTS

| JP | 60-77764 | 5/1985 |
| JP | 63-31668 | 5/1988 |
| JP | 2000-279530 | 10/2000 |

(Continued)

OTHER PUBLICATIONS

Supplemental European Search Report in counterpart application No. EP12739553, dated Aug. 12, 2015.

*Primary Examiner* — Yashita Sharma
*Assistant Examiner* — Rebecca Preston
(74) *Attorney, Agent, or Firm* — Greenblum & Bernstein, P.L.C.

(57) ABSTRACT

Provided is a stent graft that has superior prevention of endoleakage due to being resistant to creasing, and has superior prevention of graft migration as a result of promoting cell infiltration into gaps among microfibers in a dispersed state and forming an integrated structure with the cells in the landing zone of the stent. The stent graft according to the present invention is a stent graft comprising a stent graft fabric that has microfiber bundles consisting essentially of microfilaments having a filament linear density of 0.5 dtex or less, and said microfiber bundles having a total linear density of 10 to 60 dtex/120 to 3000 filaments, for the warp and/or weft, and in which the porosity of the microfiber bundles is 30% to 95%, wherein said stent graft has said stent graft fabric being located in at least 1 cm range from the central end.

8 Claims, 4 Drawing Sheets

(56) References Cited

U.S. PATENT DOCUMENTS

2007/0166540 A1 7/2007 Baba et al.
2009/0171435 A1* 7/2009 Kuppurathanam et al. .. 623/1.12

FOREIGN PATENT DOCUMENTS

| | | |
|---|---|---|
| JP | 2004-113441 | 4/2004 |
| JP | 2005-124959 | 5/2005 |
| JP | 2005-307408 | 11/2005 |
| JP | 2007-222477 | 9/2007 |
| JP | 2008-75228 | 4/2008 |
| WO | 97/17039 | 5/1997 |
| WO | 03/106518 | 12/2003 |
| WO | 2004/108146 | 12/2004 |

* cited by examiner

0# STENT GRAFTS

TECHNICAL FIELD

The present invention relates to a fabric for a stent graft (hereinafter to be simply referred to as the "fabric") having superior endoleakage prevention due to resistance to the occurrence of creasing as well as superior graft migration prevention due to the use of microfibers having superior cytophilicity, and to a stent graft that uses the fabric.

BACKGROUND ART

Stent graft surgery is a procedure performed for treatment of an abdominal aortic aneurysm or thoracic aortic aneurysm and the like that consists of inserting a tubular fabric and an expandable member contained in a sheath into an exposed blood vessel by making a small incision in the femoral region, continuing to insert until the affected region is reached, and then extending the tubular stent graft fabric with the expandable member and positioning in the blood vessel so as to span normal portions in front of and in back of the affected region so as to repair the affected region from within the blood vessel.

However, stent graft surgery still has numerous problems. An example thereof, although the portion where the stent graft fabric is to be contacted with a vessel wall and fixed thereto is referred to as the landing zone, problems may occur at this landing zone such as leakage of blood (hereinafter to be simply referred to as "endoleakage") or migration of the stent graft from the landing zone due to inadequate fixation of the stent graft fabric (hereinafter to be simply referred to as "migration").

An example of one mode of endoleakage is a phenomenon in which blood flows into an aneurysm from a gap between the stent graft and a blood vessel. This has been indicated to be caused by oversizing or looseness of the fabric at the landing zone where closest contact is to be made with the blood vessel.

In general, a tubular stent graft fabric having a diameter roughly 20% larger than the diameter of blood vessel in the landing zone of a patient is used in the clinical setting. Since a normal blood vessel wall expands in diameter by about 10% due to its flexibility, the stent graft fabric, which has ample size relative to blood vessel diameter, is pushed against the blood vessel wall and fixed in position. As a result, as is described in Patent Documents 1 and 2 indicated below, the fabric may become loose after being expanded within the blood vessel and may end up sticking up inside the blood vessel in the manner of a sail, thereby enabling blood to be guided to the inside of the sail and resulting in the occurrence of endoleakage.

Although stent grafts are pushed into a blood vessel from the sheath and pushed apart with the expandable member, the status of the fabric following fixation in the landing zone cannot be confirmed by X-ray.

In addition, as was previously described, fixation of the stent graft is dependent upon pressure applied from lumen towards the vessel inner wall by the expandable member. However, in the case of a diseased vessel wall, inner diameter gradually increases, and pressure applied to the vessel wall at the point that inner diameter has exceeded the inner diameter of the stent graft, namely, the strength that enables fixation of the stent graft, is lost. Therefore, although a fixation method has been employed by which narrow hooks attached to the expandable member are driven into the vessel wall, this is unable to completely prevent migration.

Fixation of a stent graft must be maintained throughout the life of the patient. Thus, it is necessary to provide means of continuous fixation of the fabric even if the inner diameter of a diseased blood vessel wall has expanded.

As has been described above, the prior art has not yet solved the problems of endoleakage and migration.

PRIOR ART DOCUMENTS

Patent Documents

[Patent Document 1] U.S. Pat. No. 6,352,561
[Patent Document 2] U.S. Pat. No. 6,613,072
[Patent Document 3] Japanese Unexamined Patent Publication No. S60-77764
[Patent Document 4] Japanese Unexamined Patent Publication No. S63-31668
[Patent Document 5] Japanese Unexamined Patent Publication No. 2005-124959
[Patent Document 6] Japanese Unexamined Patent Publication No. 2000-279530
[Patent Document 7] Japanese Unexamined Patent Publication No. 2005-307408
[Patent Document 8] Japanese Unexamined Patent Publication No. 2008-75228
[Patent Document 9] International Publication No. WO 2003/106518
[Patent Document 10] International Publication No. WO 2004/108146
[Patent Document 11] Japanese Unexamined Patent Publication No. 2007-222477

SUMMARY OF THE INVENTION

Problems to be Solved by the Invention

With the foregoing in view, an object of the present invention is to provide a fabric for a stent graft having superior endoleakage prevention due to being resistant to the occurrence of creasing as well as superior graft migration prevention due to the use of microfibers having superior cytophilicity, and a stent graft that uses the fabric.

Means for Solving the Problems

As a result of conducting extensive studies to solve the aforementioned problems, the inventors of the present invention found that the aforementioned problems can be solved by using fine fibers having a specific structure, thereby leading to completion of the present invention.

Namely, the present invention is as described below.

[1] A stent graft comprising a stent graft fabric that has microfiber bundles consisting essentially of microfilaments having a filament linear density of 0.5 dtex or less, and said microfiber bundles having a total linear density of 10 to 60 dtex/120 to 3000 filaments, for the warp and/or weft, and in which the porosity of the microfiber bundles is 30% to 95%, wherein said stent graft has said stent graft fabric being located in at least 1 cm range from the central end.

[2] The stent graft described in [1] above, wherein the microfiber bundles have 10 microcrimp bending points or more per centimeter.

[3] The stent graft described in [1] or [2] above, wherein the total linear density of the microfiber bundles is 20 to 60 dtex/120 to 2000 filaments.

[4] The stent graft described in [1] or [2] above, wherein the total linear density of the microfiber bundles is 20 to 60 dtex/350 to 1500 filaments.
[5] The stent graft described in any of [1] to [4] above, wherein the stent graft fabric has the stent graft fabric being located in at least 2 cm range from the central end.
[6] The stent graft described in any of [1] to [4] above, wherein the stent graft fabric has the stent graft fabric being located in at least 3 cm range from the central end.
[7] The stent graft described in any of [1] to [4] above, wherein the stent graft fabric has the stent graft fabric being located in at least 5 cm range from the central end.
[8] The stent graft described in any of [1] to [4] above, wherein the entirety is covered with the stent graft fabric.
[9] The stent graft described in any of [1] to [7], wherein the stent graft fabric has the stent graft fabric being located in at least 1 cm range from the peripheral end.
[10] The stent graft described in any of [1] to [9] above, wherein the thickness of the stent graft fabric is 20 to 90 μm.
[11] The stent graft described in any of [1] to [10] above, wherein the burst strength of the stent graft fiber as measured in accordance with a burst strength test in compliance with ANSI/AAMI standards is 10 to 30 Kg.
[12] The stent graft described in any of [1] to [11] above, wherein the flex-rigidity of the stent fabric as measured according to the cantilever bending method is 10 to 40.
[13] The stent graft described in any of [1] to [12] above, wherein the water permeability of the stent graft fabric as measured in accordance with a burst strength test in compliance with ANSI/AAMI standards is 50 to 1000 ml.
[14] The stent graft described in any of [1] to [13] above, wherein the microfibers that compose the microfiber bundles are composed of a material selected from the group consisting of polyester, polyamide, polyolefin and polytetrafluoroethylene.
[15] The stent graft described in any of [1] to [14] above, wherein the porosity of the microfiber bundles is 30% to 95% from the outside to the center of the microfiber bundles.

Effects of the Invention

The stent graft fabric according to the present invention has superior endoleakage prevention due to being resistant to the occurrence of creasing, and has superior graft migration prevention due to promoting the infiltration of cells into gaps among microfibers in a dispersed state and integrating with the cells at the landing zone of the stent graft.

BRIEF DESCRIPTION OF THE DRAWINGS

FIG. 1 is a photograph in lieu of drawing of a microfiber bundle having microcrimp bending points. The scale shown is 1 mm. The microfiber has more than 10 microcrimp bending points (arrows) per centimeter in the form of non-linear locations of bending, undulation or twisting and the like.

EMBODIMENTS OF THE INVENTION

Figure 1:
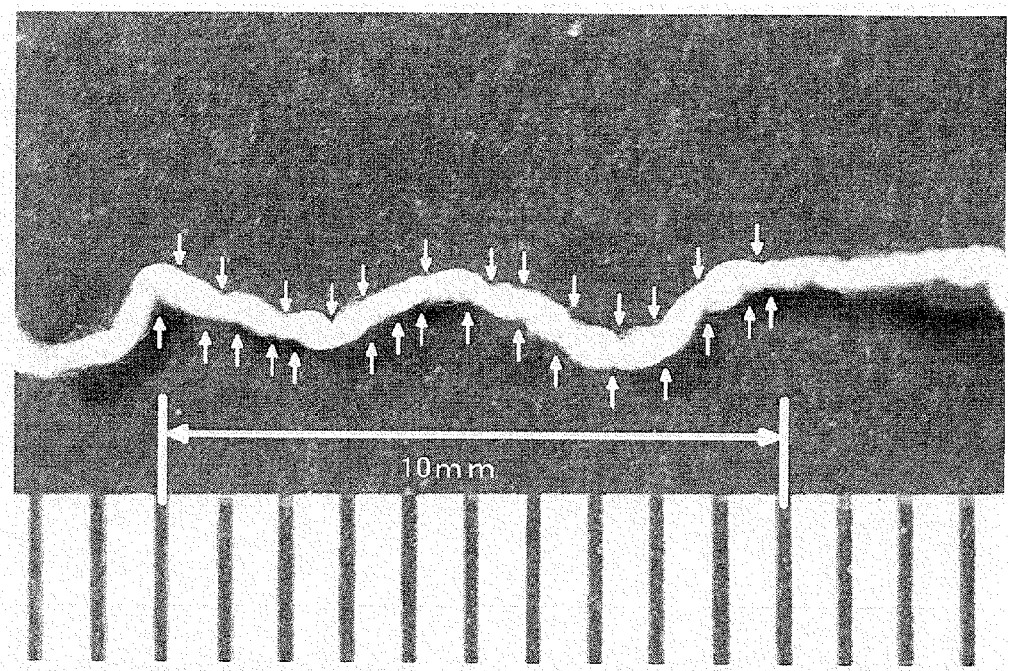

The following provides a detailed explanation of the present invention.

The invention of the present application is based on the idea of enabling a fabric to demonstrate an anchoring effect in the manner of growing roots by giving the fabric the characteristic of being resistant to the occurrence of creasing by using a multifilament yarn composed of bundles of microfibers in a dispersed state, or in other words, filaments of mutually separated microfibers, and simultaneously enabling a patient's own cells to infiltrate the gaps among filaments of the dispersed microfibers to form a structure in which the cells and microfiber filaments are integrated into a single unit.

In particular, since the stent graft fabric contacts a blood vessel of the body while directly receiving the upstream flow of blood sent from the heart at an end surface of the fabric over a range of at least 1 cm from the central end of the stent graft (namely, the end on the side of the tubular stent graft fabric closest to the heart), this range is an important site for fixation of the stent graft, and is typically referred to as a landing zone. In order to prevent leakage into the vessel lumen, or so-called endoleakage, it is essential that at least the fabric be tightly adhered to the vessel wall so that there are no gaps formed between the fabric and the vessel over this range. However, since the fabric was simply adhered to a vessel wall in the prior art, cells of the vessel wall merely surrounded the fabric in a capsular state, thereby making it difficult to integrate the tissue cells and fibers into a single unit. As a result, there was the risk of the occurrence of a phenomenon in which gaps form between the fabric and body tissue, or in other words, a phenomenon in which a positional shift occurs between the fabric and the blood vessel with the passage of time, also referred to as graft migration. When graft migration occurs, in addition to the stent graft failing to demonstrate aneurysm therapeutic effects, the patient's life may be put at risk due to interruption of arterial blood flow. In order to avoid this danger, in the present invention, the fabric is not merely adhered to a vessel wall, but rather microfibers known to impart favorable footholds for cell migration are used for the fibers that compose the fabric, and fiber bundles are given porosity required by cells so as to facilitate infiltration by cells into gaps among the fibers. As a result of employing this configuration, graft migration can be prevented by enabling the fabric to form an integrated structure with the cells, namely the vessel wall. Thus, in the fabric according to the present invention, it is necessary to use microfibers having cytophilicity and ensure that filaments of the microfibers are in a dispersed state at least over a range of 1 cm from the central end of the stent graft fabric corresponding to the landing zone.

In order to achieve the required dispersed state, the inventors of the present invention found as a result of trial and error that it is effective to use microfiber bundles having a total linear density of 10 to 60 dtex/120 to 3000 filaments consisting essentially of microfilaments having a filament linear density of 0.5 dtex or less for the warp and/or weft. Here, the term "consisting essentially of" refers to substantially not containing regular fibers. Naturally, although varying considerably according to the linear density of the regular fibers, the effects of the present invention can be achieved even if a small number of regular fibers are present, such as a number equal to 1% or less, 1.5% or less, 2% or less, 2.5% or less or at most 3% or less of the number of microfilaments. However, in the case regular fibers are present in the microfiber bundles in a substantial number, and composite fiber bundles are formed composed of microfibers and regular fibers, the effects of the present invention cannot be achieved.

Moreover, water jet treatment or false twist treatment of the microfiber bundles, which was not used in the prior art, was found to be effective. With respect to this point, the stent graft fabric according to the invention of the present application and the stent graft using that fabric did not exist prior to completion of the present invention, and are therefore novel articles.

Furthermore, although integration of a landing zone and vessel wall can be realized if the fabric of the present invention is used over a range of at least 1 cm from the central end of the stent graft fabric, the fabric of the present invention may also be used over a range of at least 2 cm, at least 3 cm, at least 4 cm or at least 5 cm from the central end, and if the fabric of the present invention is further used over a range of at least 1 cm, at least 2 cm or at least 3 cm from the peripheral end on the opposite side from the central end, integration of the landing zone and vessel wall can be realized on both ends of the fabric. Moreover, the entirety of the stent graft may be covered with the fabric of the present invention.

In general, stent graft fabrics are folded to a small size during production, pushed into a narrow sheath, sterilized, transported and stored. The amount of time from production to use is roughly 3 months to 3 years. During this time, gamma ray or autoclaving sterilization and physical and mechanical external forces such as compression are continuously applied to the fabric, resulting in the formation of irreparable creases. As a result of determining the cause of endoleakage based on animal experiments, the inventors of the present invention determined that, even if looseness is minimized, once deep creases form in the fabric, the creases are unable to be completely stretched out during expansion, thereby causing blood to continuously leak from the creased portions.

Therefore, an examination was made of requirements to be satisfied by stent graft fabric with respect to the occurrence of creasing, and the following basic requirements were placed on the fabric according to the present invention so that the stent graft fabric passed through a narrow hole so as to be inserted into a narrow sheath and so that deep creases visible to the naked eye are not formed after passing there through.

A tubular fabric having an inner diameter of 41 to 45 mm must pass through a hole having a diameter of 3.7 mm and there must be no formation of creases after passage.

A tubular fabric having an inner diameter of 36 to 40 mm must pass through a hole having a diameter of 3.3 mm and there must be no formation of creases after passage.

A tubular fabric having an inner diameter of 30 to 35 mm must pass through a hole having a diameter of 3.0 mm and there must be no formation of creases after passage.

A tubular fabric having an inner diameter of 25 to 29 mm must pass through a hole having a diameter of 2.7 mm and there must be no formation of creases after passage.

A tubular fabric having an inner diameter of 20 to 24 mm must pass through a hole having a diameter of 2.3 mm and there must be no formation of creases after passage.

A tubular fabric having an inner diameter of 15 to 19 mm must pass through a hole having a diameter of 2.0 mm and there must be no formation of creases after passage.

A tubular fabric having an inner diameter of 10 to 14 mm must pass through a hole having a diameter of 1.67 mm and there must be no formation of creases after passage.

A tubular fabric having an inner diameter of 9 mm or less must pass through a hole having a diameter of 1.35 mm and there must be no formation of creases after passage.

A stent graft fabric of the prior art currently available from the A Company was unable to satisfy the aforementioned basic requirements. In contrast, the aforementioned basic requirements can be satisfied by providing a stent graft comprising a stent graft fabric that has microfiber bundles consisting essentially of microfilaments having a filament linear density of 0.5 dtex or less, and said microfiber bundles having a total linear density of 10 to 60 dtex/120 to 3000 filaments, for the warp and/or weft, and in which the porosity of the microfiber bundles is 30% to 95%, wherein said stent graft has said stent graft fabric being located in at least 1 cm range from the central end thereof.

The inventors of the present invention focused on the use of microfibers from the viewpoint of ensuring flexibility without the occurrence of creasing. The aforementioned Patent Documents 3 to 5 disclose the use of microfibers in an artificial blood vessel for open surgery.

In addition, the aforementioned Patent Document 6 discloses that microfibers are preferable for use in a stent graft fabric. However, if microfibers are used at locations of blood vessels where tension is applied to the vessel wall by blood pressure, individual filaments become aligned and easily become closely packed, thereby making it difficult to demonstrate the surface area effects characteristic of microfiber filaments. Therefore, the aforementioned Patent Document 5 proposes dispersion, or in other words, mutual separation, of microfiber filaments by water jet treatment of false twist treatment of the microfiber filaments for the purpose of preventing the microfiber filaments from becoming closely packed.

Therefore, the inventors of the present invention carried out water jet treatment and false twist treatment using microfibers in accordance with the description of Patent Document 5. However, this treatment and texturing was not suitable for stent graft fabrics. In Patent Document 5, the ranges relating to thickness and total linear density of fiber bundles of microfibers are not defined, and thick fiber bundles are used in the examples. More specifically, examples of the fiber bundles used include those of 120d/40f f=36, 128d/32f f=16, 245d/40f f=36, 120d/40f f=36, 82d/24f f=36, 125d/50f f=70 and 220d/72f f=16. When these are represented as decitex and number of filaments, they become 107 dtex/1440 filaments, 114 dtex/512 filaments, 218 dtex/1440 filaments, 107 dtex/1440 filaments, 73 dtex/864 filaments, 111 dtex/3500 filaments and 194 dtex/1152 filaments. Even if these microfiber bundles are subjected to water jet treatment at an ordinary pressure of about 70 atm, only the fibers on the surface are dispersed, while fibers within the bundles remain undispersed. When hydraulic pressure was increased, although microfiber filaments on the surface of the fiber bundles were dispersed when the pressure exceeded 100 atm, the filaments ended up being severed. In addition, as a result of filaments being crushed inside the fiber bundles, the filaments were conversely not dispersed and gaps among filaments became smaller. Severing of the filaments caused the generation of lint and led to a decrease in mechanical strength of the fabric. In addition, the presence of flock is prohibited in medical materials used for implants. Therefore, as a result of examining conditions for obtaining an optimally dispersed state for stent graft fabric without causing microfiber filaments to be severed, it was found that the desired dispersed state can be achieved by reducing the thickness of the fiber bundles after having adjusted hydraulic pressure and determined the diameter of nozzle holes, number of repetitions, distance between nozzle holes and fabric and numerous other conditions. Namely, microfiber bundles having a total linear density of 10 to 60 dtex/120 to 3000 filaments are used in the present invention. The total linear density of the microfiber bundles is preferably 30 to 50 dtex.

Another means for dispersing microfiber filaments is false twist treatment. The use of false twist treatment is expected to also have the effect of making it difficult for creasing to occur in the fabric. Wool fabric is resistant to creasing. Twisting is present in natural wool fabric. Existing fine twists cancel out the formation of new creases. This being the case, false twist treatment of microfibers is also expected to have the effect of preventing creasing. The aforementioned Patent Document 5 describes an artificial blood vessel that uses false twist textured thread not for the purpose of solving the problem of creasing, but rather promoting the infiltration of cells into gaps among microfiber filaments. On the other hand, although the inventors of the present invention carried out false twist treatment on microfibers in accordance with Patent Document 5 for the purpose of maintaining microfiber filaments in a desired dispersed state in order to solve the problem of creasing, the following problems occurred.

In the case of ordinary false twist treatment, twists are formed at about 2000 twists per meter followed by heating, lowering the temperature and untwisting. However, it was difficult to form twists in microfibers at 2000 twists per meter. When the twisting speed was further increased, the fibers ended up rupturing, fluff formed and the thread became tangled, thereby making it impossible to wind the thread. Therefore, as a result of determining false twist treatment conditions that improve work efficiency while preventing thread breakage by carefully and gradually increasing the twisting speed and determining the twisting speed applied to the threads according to the respective characteristics of the microfibers, in the case of polyester fibers, it was necessary to give careful consideration to such factors as the degree of polymer chip crystallization, polymer viscosity of fiber, elongation, thread tension, twisting speed and temperature, and it was also determined that it is necessary to set optimum conditions when untwisting as well.

As a result of this false twist treatment procedure, small bends, namely microcrimps, were imparted to the fibers. The following provides a detailed description of this work. Microcrimps are formed by twisting the microfibers at about 3,000 to 6,000 times per meter using a twisting machine followed by untwisting.

Porosity of the fabric can be increased by modifying the manner in which the fabric is woven. More specifically, gaps among fibers are formed by microcrimping and density of reed when weaving the fabric is increased to 60 dents/cm or more to make the number of warp drawn in 2 to 8 threads. By reducing the number of threads drawn for one dent, thread unevenness is reduced and uniform gaps can be obtained. In addition, by using microcrimped thread for the microfibers of the weft, and carrying out loosely twisting at 1,000 to 3,000 times/meter on the warp, a fabric can be produced having even higher porosity.

Although the production of a plain woven fabric using microcrimped fibers was extremely difficult in the prior art, this problem was overcome in the present invention by making innovative contrivances with respect thereto. The following provides a detailed description thereof. In order to increase the total linear density of polyester fibers used for the warp and because of the use of crimped threads, after carrying out gluing by a paste consisting mainly of PVA as a countermeasure against thread breakage and fluffing during weaving, warps are prepared. Threads divided into small groups by winding around several hundred paper tubes during gluing is attached to a creel stand and wound into a beam while aligning the warp using a warping machine. Following completion of warp beaming, the beams are attached to a jacquard machine, passed through a guide, and after passing each thread through the heddle of a harness, the thread was further subjected to denting. Following completion of denting, the thread is tied at the site where threads are just being woven and placed on a winder followed by adjusting the warp tension to complete warp preparation. Weft preparation consists of winding the weft around a bobbin, placing the bobbin in a shuttle, and arranging the shuttle in a shuttle control box. Each heddle of the warp is raised and lowered by electronic control, and the weft is inserted by passing the electronically controlled shuttle through gaps in the raised and lowered warp. A thin, highly dense woven fabric having a weft density of 50 threads/cm is then produced by beating the inserted weft at the site where threads are just being woven.

During the course of this trial and error, the inventors of the present invention found that the thickness of the microfiber bundles, namely the total linear density, is important when imparting microcrimps. Partial severing occurred since microfiber filaments on the outside of the microfiber bundles are powerfully stretched if the total linear density is high. Therefore, the inventors of the present invention simultaneously solved the problem of severing of microfiber filaments while carrying out false twist treatment in excess of 2,000 twists per meter, which was not used in the prior art, by reducing the total linear density, or in other words, by making the fiber bundles narrower.

In Patent Document 5, there is no description regarding the range of total linear density of the microfibers, and thick microfibers are used in each of the examples. This is as previously described with respect to water jet treatment. Although does not describe false twist treatment at a low total linear density, the aforementioned Patent Document 8 describes that false twist treatment of 30d/10f is carried out in a portion of the steps used to produce microfibers. However, Patent Document 8 does not contain a description of detailed conditions, such as twisting speed, during false twist treatment.

In the fabric according to the present invention, it is necessary that the microfiber filaments be in a desired dispersed state from the outside to the center of the microfiber bundles, and this dispersed state can be defined by the porosity of the microfiber bundles. In the case of projecting a microfiber bundle on a flat surface, porosity of the microfiber bundles is represented by: (area occupied by microfiber bundles−area occupied by each microfiber filament)÷(area occupied by microfiber bundles)×100. More specifically, porosity can be measured by preparing a section having a thickness of 3 micrometers with a glass knife by embedding the fabric in a resin such as Technovit (Kulzer Co., Germany), photographing several locations (roughly 3 to 8) extending from the outside to the center of the microfiber bundles with a light microscope at a magnification of 400×, and calculating the ratio of the portion occupied by fibers to the portions among fibers on each photograph by measuring their respective areas followed by calculating the average value thereof. Ordinary computer software such as "NIH Image" is used for measuring image area. NIH Image is public domain software used to carry out image processing developed by Wany Rasband of the U.S. National Institute of Health (NIH), or in other words, is software that discloses a source code. This software is capable of image scanning, display, editing, emphasis, analysis, printout and animation. It is also compatible with numerous standard image processing functions (including histogram equalization, contrast enhancement, density profiling, smoothing, edge detection, median filtering, space overlapping and calculation of area ratios). In the field of medicine, this software is typically used for cell counting, electrophoresis band analysis, analysis of bone and other X-ray images and analysis of various medical and biological images. In the present invention, porosity obtained by measuring using J Soft that is packed with this software is 30% to 95%.

Porosity of 30% to 95% as calculated in the present invention represents the porosity from the outside to the center of the microfiber bundles. In contrast, although porosity near the outside is higher in microfiber bundles obtained by fiber raising treatment and the like of the prior art, porosity near the center remained equal, and it is not possible to increase porosity beyond 30%.

As a result of studying conditions for carrying out false twist treatment on narrow bundles of microfibers in order to create in which microfiber filaments are dispersed at a porosity of 30% to 95%, false twist treatment conditions were found for microfibers that ultimately prevented the occurrence of thread breakage by using microfiber bundles having a total linear density of 60 dtex or less that were used in the study of water jet treatment conditions. Twisting speed during false twist treatment was able to be increased from 2500 twists to 5000 twists per meter without incident provided the total linear density was 60 dtex or less. The twisting speed is preferably 3000 to 4000 twists per meter.

The fabric according to the present invention is a woven fabric or knit fabric of microfibers in which the porosity of microfiber bundles is 30% to 95% obtained by water jet treatment or false twist treatment of microfiber bundles having a total linear density of 10 to 60 dtex/120 to 300 filaments, and the microfiber bundles preferably have 10 or more microcrimp bending points per centimeter. This means that the microfiber bundles have 1 or more microcrimp bending points per millimeter on average. When the degree of processing is actually observed with a magnifying glass by cutting out a portion of the microfiber bundles subjected to false twist processing under the previously described conditions and placing in a natural state, the microfiber bundles that form a fabric having high resistance to creasing had 10 or more microcrimps per centimeter. Microcrimps are described in detail in the aforementioned Patent Document 7.

In the present specification, the number of microcrimp bending points is counted by placing the fabric undisturbed in a state in which tension is not applied to the threads, observing with a magnifying glass at a magnification of 10×, and using the average number of microcrimp bending points at five locations as the number of microcrimps. Microcrimp bending points refer to bending points such as bends, undulations, arcs, coils, twists, warps, zigzags, protrusions, indentations or vortexes where the microfibers are in a non-linear state. For example, in the case crimps are in the form of undulations, inflection points in the undulations are referred to as bending points, while in the case crimps are in the form of coils, those points where the coil is wound 180° from an arbitrary starting point are defined as bending points, and bending points are defined as subsequently being present each time the coil is wound 180°. FIG. 1 shows a microfiber bundle having microcrimps.

Although the warp and/or weft of the fabric of a landing zone portion, namely at least 1 cm range from the central side of the stent graft fabric, is to be essentially composed of the previously described microfiber bundles, fibers of regular thickness can be present at other sites from the viewpoint of strength and the like. In this sense, the content of microfiber bundles in the entire fabric of the landing zone portion is at least 20% by weight.

Since individual fibers of the microfiber bundles used in one embodiment of the present invention have microcrimps applied by heat treatment, even after having strongly compressed, the fibers become zigzagged and the gaps among fibers open up due to the function of the microcrimps once the compression is released. Stent grafts are folded up in a tightly compressed state in a sheath until they are deployed within a blood vessel. Thus, the porosity of the fabric is low as a result of the fibers being closely packed. However, once deployed within a blood vessel, the fabric attempts to immediately return to the high level of porosity it previously had. This characteristic differs from that of the prior art. When a fabric of the prior art is placed in a state of low porosity as a result being tightly compressed and pushed together causing it to be closely packed, even if the entire fabric is deployed and compression on the fibers is released, the microfibers tend to maintain a compressed state, thereby resulting in the problem of the low porosity being the result of a closely packed state attributable to this mechanism. This problem is able to be solved by an embodiment of the present invention.

Microfiber filaments being in a dispersed state contribute to the fabric not only from the viewpoint of not forming creases, but also from the viewpoint of fixing the fabric to a vessel wall.

As was previously described, in a fabric that uses microfiber bundles having crimps and a fabric that has undergone the aforementioned water jet treatment and the like, the microfiber filaments are in a dispersed state. Therefore, cell culturing and animal implantation were carried out followed by observing the fabric on which numerous cells grew and measuring porosity at sites where microfiber bundles were present in order to determine the optimal dispersed state. Porosity was measured by preparing sections having a thickness of 3 μm with a glass knife by embedding the fabric in a resin such as Technovit (Kulzer Co., Germany), photographing with a light microscope at a magnification of 400×, and calculating the ratio of fiber bundles to the gaps among the fiber filaments by measuring their respective areas. Ordinary computer software such as "NIH Image" was used for measuring image area.

As a result of measurement, infiltration of cells into the gaps among fiber filaments was favorable if porosity was 30% or more. If porosity is less than 30%, the gaps among fiber filaments become excessively small and closely packed, thereby making it difficult for cells to infiltrate therein. On the other hand, if porosity exceeds 95%, the fabric loses its shape. Thus, in the fabric according to the present invention, microfiber bundles are required to have an optimum porosity of 30% to 95%.

Sections were prepared by embedding a fabric produced from microfiber bundles having 10 or more microcrimps per centimeter in a resin, the sections were observed with a light microscope at a magnification of 400×, photographs of the sections were taken, and the area occupied by the microfiber bundles and the area occupied by gaps among fiber filaments were calculated. In addition, fabric that underwent water jet treatment or false fiber texturing was simultaneously examined. As a result, in the case of using microfiber bundles having a total linear density of 10 to 60 dtex/120 to 3000 filaments, porosity was within the range of 30% to 95% if microfiber bundles were used that had 10 or more microcrimp bending points per centimeter, water jet treatment was carried out, or false twist treatment was carried out.

Although microfiber bundles having a filament linear density of 0.5 dtex or less and total linear density of 10 to 60 dtex/120 to 3000 filaments are used in the fabric according to the present invention, a study was also conducted regarding the suitable number of filaments, namely the fineness of microfiber filaments, for this total linear density of 10 to 60 dtex. If total linear density has been determined, then the diameter of individual microfiber filaments is determined by the number of filaments. In general, the flexibility of a fabric is said to be proportional to the fourth power of the diameter of the fibers used, and the smaller diameter the fiber filaments have, the greater flexibility of the fabric is obtained. Therefore, it is thought to be more advantageous to use fine fiber filaments, as a result of studying the relationship with cells in the present invention, since cells infiltrate the gaps among fiber filaments by using microfiber filaments as suitable footholds. If fiber filaments are excessively fine in the manner of 0.003 dtex as obtained by electrostatic spinning, however, a phenomenon has been confirmed in which cells are unable to grab onto the fiber filaments for use as footholds, but rather incorporate the fiber filaments within the cells as if they were phagocytizing the fiber filaments. Thus, fiber filaments that are excessively fine are unable to serve as footholds for guiding cells. In addition, although the aforementioned Patent Documents 9 and 10 describe methods for removing white blood cells using fine fibers and state that the microfibers have superior cytophilicity, there are no descriptions relating to the type of cells or optimum size of the fibers. In the present invention, from the viewpoint of cytophilicity, the thickness of individual fiber filaments was found to preferably be 0.5 dtex or less and particularly preferably 0.1 dtex or less, while from the viewpoint of water jet treatment and false twist treatment, total linear density was determined to preferably be 10 to 60 dtex, and in consideration thereof, total linear density of 10 to 60 dtex/120 to 3000 filaments was determined to be optimal. Thus, in the fabric according to the present invention, in the case of a total linear density of 10 to 60 dtex, the total number of filaments is 120 to 3000, microfibers of 20 to 60 dtex/120 to 2000 filaments are preferable, and microfibers of 20 to 60 dtex/350 to 1500 filaments are more preferable.

In the present invention, false twist treatment is carried out using microfiber bundles spun by direct spinning. Other examples of methods used to produce the microfibers include island-in-sea or split types. These methods are characterized by forming a fabric with thick fibers comparable to regular fibers followed by expressing the fibers as microfibers by solvent extraction or heating treatment carried out in a post-processing step. Thus, false twist treatment is presumed to be able to be carried out easily by twisting these fibers while still in the state of thick fibers of the island-in-sea type or split type. Therefore, false twisting was carried out using fibers having an island-in-sea structure, considered to be the most typical among these fibers. As a result, it was not possible to impart at least one or more microcrimps per millimeter. At most, microcrimps were only able to be imparted at the rate of 1 per 2 millimeters, and the resulting crimps only had gentle curves. Namely, in the case of the island-in-sea type, fine false twists are unable to be imparted, making it difficult to impart microcrimps as expected since twisting is carried out while still containing styrene and polyester copolymers.

In addition to striving to eliminate the problem of endoleakage by not allowing the formation of creases in the fabric, another object of the present invention is permanent fixation of the fabric at the landing zone. As a result of repeating animal studies using commercially available fabric produced in accordance with the prior art, vessel wall tissue and the fabric were clearly determined not to maintain an integrated structure following the passage of a long period of time. Although fabric made of e-PTFE or tightly woven polyester fibers is used in the clinical setting, patient cells are not incorporated in the fabric wall in either case. As a result, the fabric is in a dissociated state from the body tissue, and such dissociated state was clearly determined in the present invention to cause migration.

Moreover, the inventors of the present invention also determined that fixation strength is lost if cracks form in a vessel wall at the locations of hooks used to fix the stent graft to a vessel wall. A phenomenon is well known in which, when narrow wires are attached to a piece of ice and gravity is applied to the ice, the wires gradually move through the ice. Since diseased vessel walls were stretched easily, it is not difficult to imagine that narrow hooks would cut and move through such a vessel wall when subjected to a continual force. A phenomenon is also known by which suturing thread used to anastomose an artificial vessel gradually cuts through a vessel wall and ends up moving over a long period of time. These can be caused by migration.

Therefore, the inventors of the present invention conceived of a fabric in which microfiber filaments contact a landing zone in a dispersed state. As a result of the microfiber filaments being present with the vessel wall in a dispersed state, cells are guided to gaps among the fiber filaments and are able to infiltrate there among, thereby resulting in the formation of a structure in which the cells and microfiber filaments are integrated into a single structure and allowing the demonstration of anchoring effects in the manner of growing roots, and the present invention provides this technical idea that is not known in the prior art.

The aforementioned desired effect is demonstrated by using a fabric produced with microcrimped microfiber bundles obtained by carrying out water jet treatment or false fiber texturing under specific conditions on microfiber bundles having a specific structure. As a result of actually conducting animal studies using this fabric, a structure was confirmed to have been formed in which the cells were integrated into a single structure with the fabric.

Although fabric of the landing zone portion is to be composed of microfiber bundles having microcrimps as previously described, from the viewpoints of strength and the like, fibers of ordinary thickness can also be incorporated. In the present invention, from the viewpoint of demonstrating the effect of these microfiber bundles, the content of microfiber bundles in the entire fabric is preferably at least 20% by weight.

The fabric according to the present invention may be a woven fabric or knit fabric provided the content of the microfiber bundles in the entire fabric is at least 20% by weight. In addition, any weaving method or knitting method may be used. However, as indicated in the following examples, the fabric according to the present invention is preferably a plain woven fabric that uses the aforementioned microfiber bundles for the weft. The fabric according to the present invention is naturally also required to satisfy the requirements stent graft fabrics of being lightweight, strong and flexible, and not allowing leakage of blood.

More specifically, in the fabric according to the present invention, the thickness of the stent graft fabric is preferably 20 to 90 μm, the burst strength of the stent graft fiber as measured in accordance with a burst strength test in compliance with ANSI/AAMI standards is 10 to 30 Kg, the flex-rigidity of the stent fabric as measured according to the cantilever bending method is 10 to 40, or the water permeability of the stent graft fabric as measured in accordance with a burst strength test in compliance with ANSI/AAMI standards is 50 to 1000 ml.

In addition, although the stent graft fabric according to the present invention is processed in the shape of a tube, during the application thereof, the width of the landing zone is required to a length of 1 cm or more from the end of the stent graft fabric. If the length is less than 1 cm, fixation strength becomes weak. In clinical applications as well, a stent graft is not used unless a landing zone of 1 cm or more can be secured. If the gaps among microfiber filaments extend over a prescribed range over the entire surface of a landing zone having a length of 1 cm or more, a structure is formed in which cells and fiber filaments are integrated into a single structure. This type of fixation is more reliable since the surface area is considerably larger than fixation using hooks of the prior art. In particular, after a long period of time has elapsed, tissue formed by fibroblasts results in strong fixation with the passage of time due to a gradual increase collagen fibers. Since this tissue has been produced by the body, it is maintained and managed by the body itself. In other words, the patient's body per se serves to fix the stent graft fabric and maintains the fabric for the duration of the patient's life.

The formation of tissue in which cells and fibers are integrated into a single structure at a landing zone eliminates the formation of gaps between the fabric and vessel wall. Namely, in the present invention, by dispersing microfiber filaments of 0.5 dtex or less, preferably 0.3 dtex or less and more preferably 0.1 dtex or less, the problems of endoleakage and migration can be solved simultaneously.

The material of the microfiber filaments that compose the aforementioned microfiber bundles used in the fabric according to the present invention may be any material that is suitable for ordinary implantation. However, the material of the microfiber filaments is preferably selected from the group consisting of polyester, polyamide, polyolefin and polytetrafluoroethylene based on the proven results of these materials.

The fabric according to the present invention is used as a stent graft (stent-type artificial blood vessel) by combining with an expandable member (stent). Self-expanding materials using a shape memory alloy, superelastic metal or synthetic polymer material can be used for the expandable member. The expandable material may employ any design of the prior art. A type that is expanded with a balloon may be applied for the self-expandable member instead of a self-expanding type.

Although the following provides a detailed explanation of the present invention through examples thereof, the invention of the present application is not limited to these examples.

EXAMPLES

In the following examples, microfiber bundles having a total linear density of 52 dtex/350 filaments (manufactured by Asahi Kasei Fibers Corp.) were used as a typical example of microfiber bundles having a total linear density of 10 to 60 dtex/120 to 3000 filaments used in the fabric according to the present invention. Fibers having a total linear density of 34 dtex/24 filaments were used as regular fibers that are not microfibers. In addition, microfibers having a total linear density of 218 dtex/1440 filaments were used as microfibers of bundles having a total linear density outside the range of the total linear density of 10 to 60 dtex/120 to 3000 filaments used in the fabric according to the present invention. Polyester, which is commonly used in stent graft fabrics, was selected for the material of the microfibers.

Comparative Example 1

A plain woven tubular fabric having an inner diameter of 32 mm was produced by using regular fibers having a total linear density of 34 dtex/24 filaments for the warp and using microfibers having a total linear density of 52 dtex/350 filaments for the weft. This fabric was designated as fabric A-1. When the water permeability of the fabric A-1 was measured in accordance with ANSI/AAMI standards, it was found to be 470 ml, burst strength as measured in accordance with ANSI/AAMI standards (burst test) was 16.6 kg, tear strength as measured in accordance ANSI/AAMI standards (suture retention test) was 0.69 kg, and thickness was 70 μm. Observation of the fabric with a scanning electron microscope (SEM) revealed that the microfibers were aligned in the form of bundles, and the gaps between fiber filaments were about 5 μm. When the fabric was embedded in Technovit resin, cut into 3 μm sections with a glass knife and the microfiber portions were photographed with a light microscope at a magnification of 400×, porosity as calculated from the ratio of the areas of the fiber bundles and the gaps among the fiber filaments using NIH Image software was 26%. The fabric was then tested for the previously described "basic requirements" placed on the fabric by the present invention. Since the fabric A-1 had a diameter of 32 mm, it must be able to pass through a hole having a diameter of 3.0 mm. The fabric A-1 passed through this hole and further passed through a narrower hole having a diameter of 2.3 mm. However, well-defined creases formed in the fabric after passing through the hole as a result of observing with the naked eye.

Example 1

Water jet treatment at a hydraulic pressure of 70 atm was carried out on the fabric A-1 produced in Comparative Example 1. The resulting fabric was designated as fabric A-2. The water permeability of the fabric A-2 as measured in accordance with ANSI/AAMI standards was 378 ml, burst strength as measured in accordance with ANSI/AAMI standards (burst test) was 16.8 kg, tear strength as measured in accordance ANSI/AAMI standards (suture retention test) was 0.82 kg, and thickness was 72 µm. Observation of the fabric with a scanning electron microscope (SEM) revealed that the microfibers were separated. Although gaps between fiber filaments varied at about 30 µm to 100 µm, the fiber filaments were adequately dispersed. When the fabric was embedded in resin to prepare sections and cross-sections containing microfiber bundles were observed, the microfiber filaments were observed to be in a dispersed state and large gaps were observed between the fiber filaments. Porosity of the microfiber bundles was calculated to be an average of 91%. Next, this fabric A-2 was then tested for the "basic requirements" placed on the fabric by the present invention. Since the fabric A-2 had a diameter of 32 mm, it must be able to pass through a hole having a diameter of 3.0 mm. The fabric A-2 passed through this hole and further passed through a narrower hole having a diameter of 2.3 mm. There were no creases observed in the fabric after passage as a result of observing with the naked eye.

Comparative Example 2

A plain woven tubular fabric having an inner diameter of 32 mm was produced by using regular fibers having a total linear density of 34 dtex/24 filaments for the warp and using microfibers having a large total linear density in the form of microfibers having a total linear density of 218 dtex/1440 filaments for the weft. This fabric was designated as fabric B-1. When the water permeability of the fabric B-1 was measured in accordance with ANSI/AAMI standards, it was found to be 370 ml, burst strength as measured in accordance with ANSI/AAMI standards (burst test) was 19.6 kg, tear strength as measured in accordance ANSI/AAMI standards (suture retention test) was 0.72 kg, and thickness was 150 Observation of the fabric with a scanning electron microscope (SEM) revealed that the microfibers were aligned in the form of bundles, and the largest gaps between fiber filaments were about 5 µm, with nearly all of the microfiber filaments not having any gaps between the fiber filaments. Porosity of the microfiber bundles as determined by photographing the microfiber bundles was calculated to be an average of 28%. The fabric was then tested for the "basic requirements" placed on the fabric by the present invention. Since the fabric B-1 had a diameter of 32 mm, it must be able to pass through a hole having a diameter of 3.0 mm. Although the fabric B-1 barely passed through, well-defined creases formed in the fabric after passing through the hole as a result of observing with the naked eye.

Comparative Example 3

Water jet treatment at a hydraulic pressure of 70 atm was carried out on the fabric B-1 produced in Comparative Example 2. The resulting fabric was designated as fabric B-2. The water permeability of the fabric B-2 as measured in accordance with ANSI/AAMI standards was 320 ml, burst strength as measured in accordance with ANSI/AAMI standards (burst test) was 19.9 kg, tear strength as measured in accordance ANSI/AAMI standards (suture retention test) was 1.11 kg, and thickness was 230 µm. Observation of the fabric with a scanning electron microscope (SEM) revealed that the fiber filaments were dispersed on the surface of the microfiber bundles, and the widest gaps between the fiber filaments was about 50 µm. As a result of embedding the fabric B-2 in Technovit resin, preparing sections having a thickness of 3 µm and observing microscopically, although fiber filaments were dispersed on the surface of the microfiber bundles, they were not dispersed at all inside the fiber bundles. In addition, although porosity near the surface of the microfiber bundles was about 60%, porosity in other portions of the microfiber bundles as well as the central portions was about 26%. In other words, water jet treatment at a hydraulic pressure of about 70 atm was inadequate for dispersing the fiber filaments of thick microfiber bundles. This fabric was then tested for the "basic requirements" placed on the fabric by the present invention. Since the fabric B-2 had a diameter of 32 mm, it must be able to pass through a hole having a diameter of 3.0 mm. Although the fabric B-2 barely passed through, well-defined creases formed in the fabric after passing through the hole.

Comparative Example 4

Water jet treatment at a hydraulic pressure of 100 atm was carried out on the fabric B-1 produced in Comparative Example 2. The resulting fabric was designated as fabric B-3. As a result of subsequently observing this fabric with a scanning electron microscope (SEM), although a portion of the microfiber filaments were dispersed, detailed observation of the fibers revealed that the microfiber filaments were partially ruptured. Moreover, the microfiber filaments were only dispersed on the surface of the microfiber bundles. Therefore, as a result of embedding the fabric B-3 in Technovit resin, preparing sections having a thickness of 3 µm and observing with a light microscope for the sake of confirmation, although fiber filaments were dispersed near the surface of the microfiber bundles and porosity was 76%, they were not dispersed inside the fiber bundles and porosity was 24%. In other words, the fiber filaments were only dispersed on the surface, and were conversely closely packed in the central portions of the microfiber bundles. Thus, water jet treatment at a hydraulic pressure of about 100 atm was unsuitable for dispersing the fiber filaments of thick microfiber bundles, and the fiber filaments were clearly observed to have been severed.

Example 2

Microfiber bundles having a total linear density of 52 dtex/350 filaments were selected, and false twist treatment was carried out at 4000 twists per meter. Optimum conditions during texturing, including thread tension, twisting speed, temperature and humidity, were selected empirically. False-twisted microfiber bundles were obtained with this procedure. Following false twist treatment, as a result of observing the fibers with a magnifying glass having a magnification of 10× without applying tension to the fibers and counting the number of crimps, fine crimps (microcrimps) were observed at the rate of about 25 per centimeter. These textured fibers are referred to as microcrimped microfiber bundles. FIG. 1 shows a photograph of a microcrimped microfiber bundle.

A plain woven tubular fabric having an inner diameter of 32 mm was produced by using regular fiber bundles having a total linear density of 34 dtex/24 filaments for the warp and using microcrimped microfiber bundles produced according to the aforementioned false twist treatment for the weft. This fabric was designated as fabric C-1. When the water permeability of the fabric C-1 was measured in accordance with ANSI/AAMI standards, it was found to be 311 ml, burst strength as measured in accordance with ANSI/AAMI standards (burst test) was 17.1 kg, tear strength as measured in accordance ANSI/AAMI standards (suture retention test) was 0.69 kg, and thickness was 72 µm. Observation of the fabric with a scanning electron microscope (SEM) revealed that the microfibers were separated, and gaps between the fiber filaments ranged from 10 to 200 μm. When the fabric was embedded in Technovit resin, those portions containing microfiber bundles were photographed, and porosity was calculated from the ratio of the areas of the fiber bundles and gaps among the fiber filaments, porosity was found to be 89%. The fabric was then tested for the "basic requirements" placed on the fabric by the present invention. Since the produced fabric C-1 had a diameter of 32 mm, it must be able to pass through a hole having a diameter of 3.0 mm. The fabric C-1 passed through this hole and further passed through a narrower hole having a diameter of 2.3 mm. There were no creases observed in the fabric after passage as a result of observing with the naked eye.

Comparative Example 5

False twist treatment was carried out at 2000 twists per meter in accordance with conditions commonly used in the prior art on microfiber bundles having a total linear density of 52 dtex/350 filaments. When the fibers were observed following texturing, twisting was incomplete and when a small amount of tension was applied, the fibers became similar to straight fibers. Microcrimps were present at about 3 to 8 per centimeter, and sites containing twists and sites containing hardly any twists were irregularly jumbled together. Twisting was weak and the false twists were lost when a small amount of force was applied. When applied to a loom, a certain degree of tension was applied, the effect of false twist treatment disappeared even with that degree of tension. Therefore, when applied to a loom, the results were hardly any different from fiber bundles not subjected to false twist treatment. Thus, false twist treatment at 2000 twists per meter was determined not to demonstrate the effects of the false twists.

Comparative Example 6

Microfibers having a large total linear density in the form of microfiber bundles having a total linear density of 218 dtex/1440 filaments, which are outside the range of the total linear density of 10 to 60 dtex/120 to 3000 filaments used in the fabric according to the present invention, were selected, and false twist treatment was carried out at 4000 twists per meter. Optimum conditions during texturing, including thread tension, twisting speed, temperature and humidity, were selected empirically. Thread breakage occurred successively during the course of texturing, the thread fragments became entangled during winding, and was unable to be wound. Namely, the use of thick microfiber bundles resulted in the occurrence of thread breakage and prevented false twist treatment from being carried out.

Comparative Example 7

Microfiber bundles having a total linear density of 70 dtex/840 filaments were selected, and false twist treatment was carried out at 4000 twists per meter. Optimum conditions during texturing, including thread tension, twisting speed, temperature and humidity, were selected empirically. Although twisting speed was increased gradually without being excessive, thread breakage was observed in the step in which the thread was wound up after carrying out false twist treatment. In addition, there was also thread breakage when subsequently winding onto a small spool used in a loom, and the thread was unable to be wound. Namely, thread breakage even occurred in the case of microfiber bundles having a total linear density of about 70 dtex, and was determined to cause difficulties in false twist treatment.

Comparative Example 8

A stent graft fabric currently used in the clinical setting was acquired, and was cut into the shape of a tube having a diameter of 3.2 cm for measurement. This fabric was designated fabric D-1. The fabric D-1 was flattened by calendering. When the fabric D-1 was observed with an SEM, monofilaments were found to be used as fibers, and the gaps between fibers were a maximum of about 50 μm and a minimum of 5 μm or less. The water permeability of the fabric D-1 as measured in accordance with ANSI/AAMI standards was 270 ml, burst strength as measured in accordance with ANSI/AAMI standards (burst test) was 24.6 kg, and thickness was 80 μm. When the fabric was then tested for the "basic requirements" placed on the fabric by the present invention, since the fabric D-1 had a diameter of 32 mm, it must be able to pass through a hole having a diameter of 3.0 mm. However, the fabric D-1 was unable to pass through this hole, and was barely able to pass through a larger hole having a diameter of 3.3 mm. Well-defined deep creases were formed in the fabric after passage as a result of observing with the naked eye.

Results of comparing the fabric produced in Examples 1 and 2 with the fabrics produced in Comparative Example 1 to 3 and Comparative Example 8 are shown in the following Table 1.

TABLE 1

| | Comparative Example 8 Fabric D-1 Commercially Available | Comparative Example 1 Fabric A-1 Microfibers | Example 1 Fabric A-2 Microfibers | Comparative Example 2 Fabric B-1 Microfibers | Comparative Example 3 Fabric B-2 Microfibers | Example 2 Fabric C-1 Microfibers |
|---|---|---|---|---|---|---|
| Woven Structure | 4-4 twill | Plain weave | Plain weave | Plain weave | Plain weave | Plain weave |
| Thread type | Monofilament | Multifilament | Multifilament | Multifilament | Multifilament | Multifilament |
| Warp (total linear density) | Monofilament 10-14 dtex/1f | Regular fiber (RF) 34T24f | Regular fiber (RF) 34T24f | Regular fiber (RF) 34T24f | Regular fiber (RF) 34T24f | Regular fiber (RF) 34T24f |
| Weft (total linear density) | Monofilament 10-14 dtex/1f | Microfiber (MF) 52T350f | Microfiber (MF) 52T350f | Microfiber (MF) 218 dtex/1440 f | Microfiber (MF) 218 dtex/1440 f | Microfiber (MF) 52T350f microcrimped |
| Filament linear density | 10-14 dtex | MF 0.15 dtex RF 1.4 dtex | MF 0.15 dtex RF 1.4 dtex | MF 0.15 dtex RF 1.4 dtex | MF 0.15 dtex RF 1.4 dtex | MF 0.15 dtex RF 1.4 dtex |
| Warp density | 260/cm | 52/cm | 52/cm | 52/cm | 52/cm | 52/cm |
| Weft density | 190/cm | 35/cm | 36/cm | 30/cm | 30/cm | 37/cm |

TABLE 1-continued

| | Comparative Example 8 Fabric D-1 Commercially Available | Comparative Example 1 Fabric A-1 Microfibers | Example 1 Fabric A-2 Microfibers | Comparative Example 2 Fabric B-1 Microfibers | Comparative Example 3 Fabric B-2 Microfibers | Example 2 Fabric C-1 Microfibers |
|---|---|---|---|---|---|---|
| Microfiber bundle porosity | | 26% | 91% | 28% | 26% | 89% |
| Thickness (μm) | 80 | 70 | 72 | 240 | 230 | 72 |
| Treatment/ processing | Calendering | | Water jet treatment | | Water jet treatment | False twist treatment |
| Burst strength (kg) | 24.6 | 16.6 | 16.8 | 19.6 | 19.9 | 17.1 |
| Tear strength (kg) | 1.94 | 0.69 | 0.82 | 0.72 | 1.11 | 0.69 |
| Water permeability | 270 cc/min/cm² | 470 cc/min/cm² | 378 cc/min/cm² | 370 cc/min/cm² | 320 cc/min/cm² | 311 cc/min/cm² |
| Foldability 32φ | Passed 10 French (3.3 mm) | Passed 7 French (2.3 mm) | Passed 7 French (2.3 mm) | Passed 7 French (2.3 mm) | Passed 7 French (2.3 mm) | Passed 7 French (2.3 mm) |
| Restoration after folding | Poor, creases after passage | Good, shallow creases | Good, no creases | Poor, creases after passage | Poor, creases after passage | Good, no creases |

Comparative Example 9

A 5 cm portion of the fabric D-1 having an inner diameter of 32 mm used in Comparative Example 8 was removed, and attempted to be inserted into a sheath. As described in Comparative Example 8, although the fabric was able to pass through a hole having an inner diameter of 3.3 mm, it was unable to be inserted into the tubular sheath. Therefore, the smallest sheath into which the fabric was able to be somehow inserted was selected, and the fabric was inserted into a 12 French (4.0 mm) sheath. This state was referred to as "sheath-inserted fabric D-1".

Example 3

A 5 cm portion of the fabric A-2 having an inner diameter of 32 mm was removed and attempted to be inserted into a sheath. Although the fabric tightly fit into a 7 French (2.3 mm) sheath, it was easily able to be inserted into an 8 French (2.7 mm) sheath. In order to compare with the sheath-inserted fabric D-1 described in Comparative Example 9, the fabric A-2 was inserted into a 12 French sheath. This state was referred to as "sheath-inserted fabric A-2".

Figure 2:
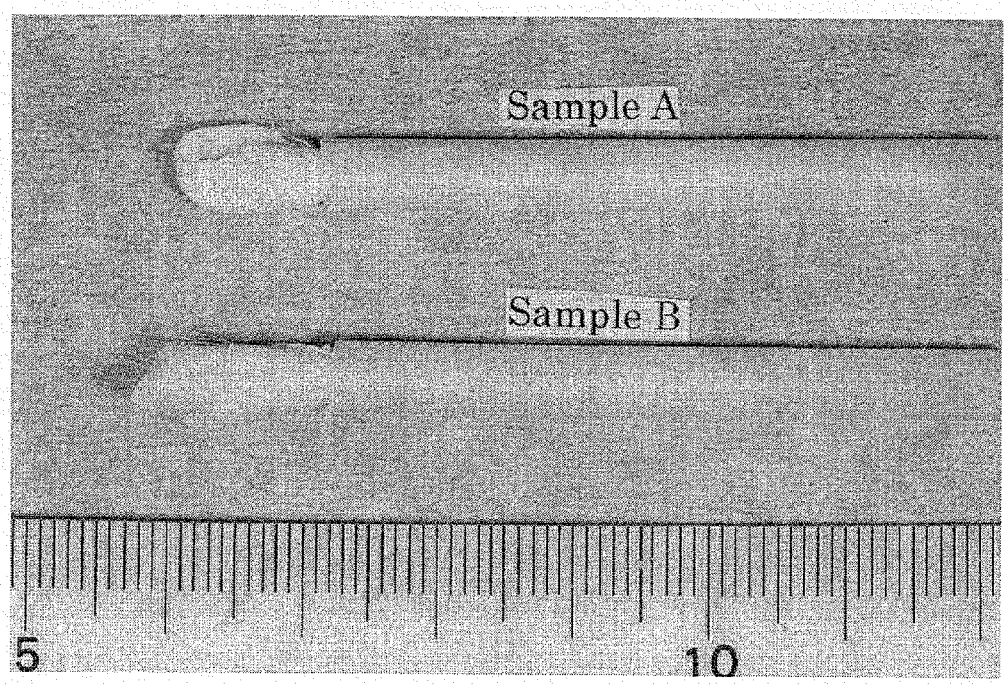
FIG. 2 is a photograph in lieu of drawing showing two types of fabrics inserted into sheaths having an inner diameter of 4 mm (12 French). Sample A is a fabric according to the present invention, while Sample B is a commercially available stent graft fabric of the prior art used in Comparative Example 7. The scale shown is 1 mm.
Figure 3:
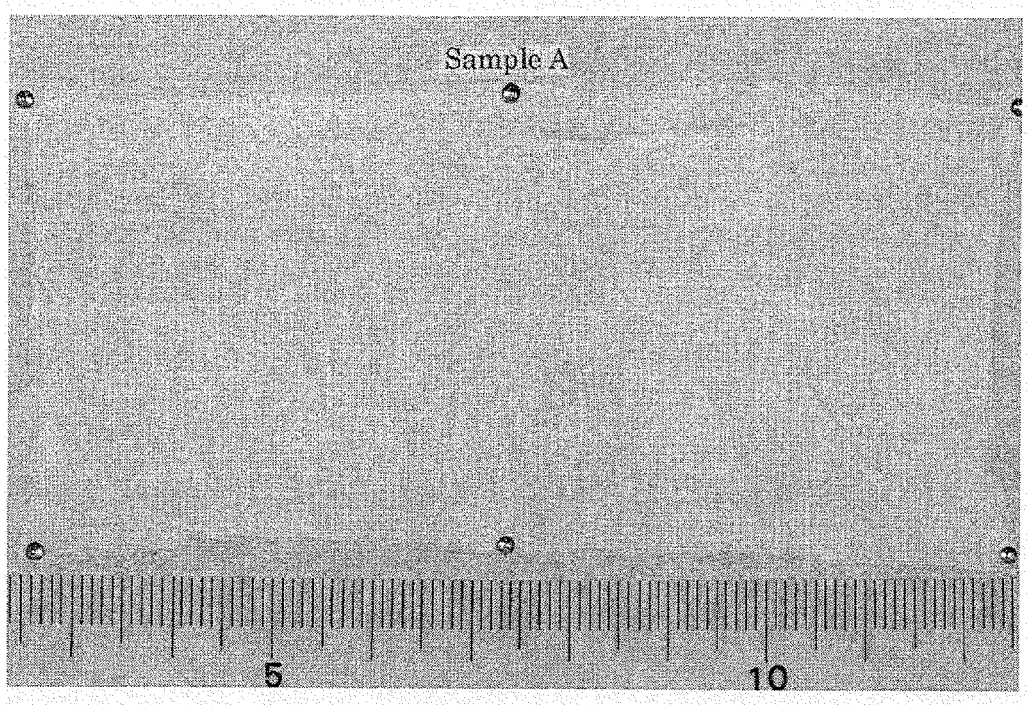
FIG. 3 is a photograph in lieu of drawing of a state in which the fabric according to the present invention of Sample A has been spread out after removing from the sheath shown in FIG. 2. Creases are not observed.
Figure 4:
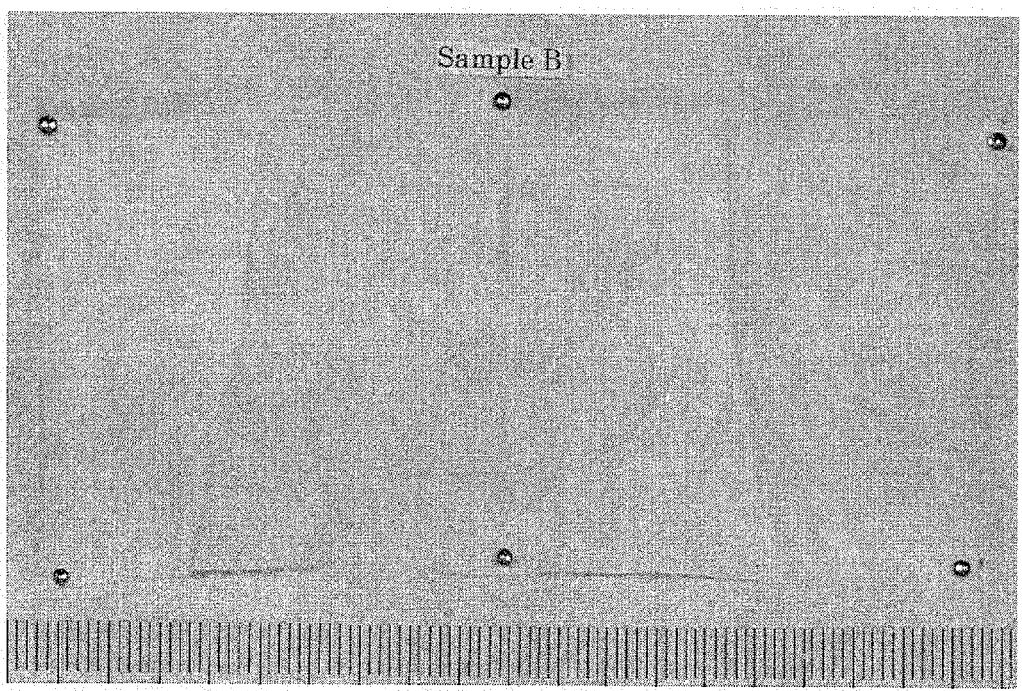
FIG. 4 is a photograph in lieu of drawing of a state in which a commercially available stent graft fabric of the prior art of Sample B has been spread out after removing from the sheath shown in FIG. 2. Deep creases can be seen.

The aforementioned "sheath-inserted fabric A-2" and "sheath-inserted fabric D-1" are shown in FIG. 2. The sheath-inserted fabrics were subsequently sterilized by autoclaving for 20 minutes at 121° C., after which the fabrics were removed from the sheaths and spread out, the states at that time being respectively shown in FIGS. 3 and 4. Sample A indicates the "sheath-inserted fabric A-2", while Sample B indicates the "sheath-inserted fabric D-1". After autoclaving, although lines in the manner of shallow creases were able to be observed in the fabric A-2 of Sample A as shown in FIG. 3, these were merely due to gathering of the fabric and were able to be removed by pressing with a finger. In contrast, the fabric D-1 of Sample B was in a state after autoclaving such that the cloth was balled up and difficult to stretch. Therefore, when the tubular fabric was cut open and spread out, deep creases were clearly found to have formed as shown in FIG. 4. As a result, although the fabric according to the present invention was determined to be resistant to creasing, the commercially available product according to the prior art was found to form creases.

Example 4

Figure 5:
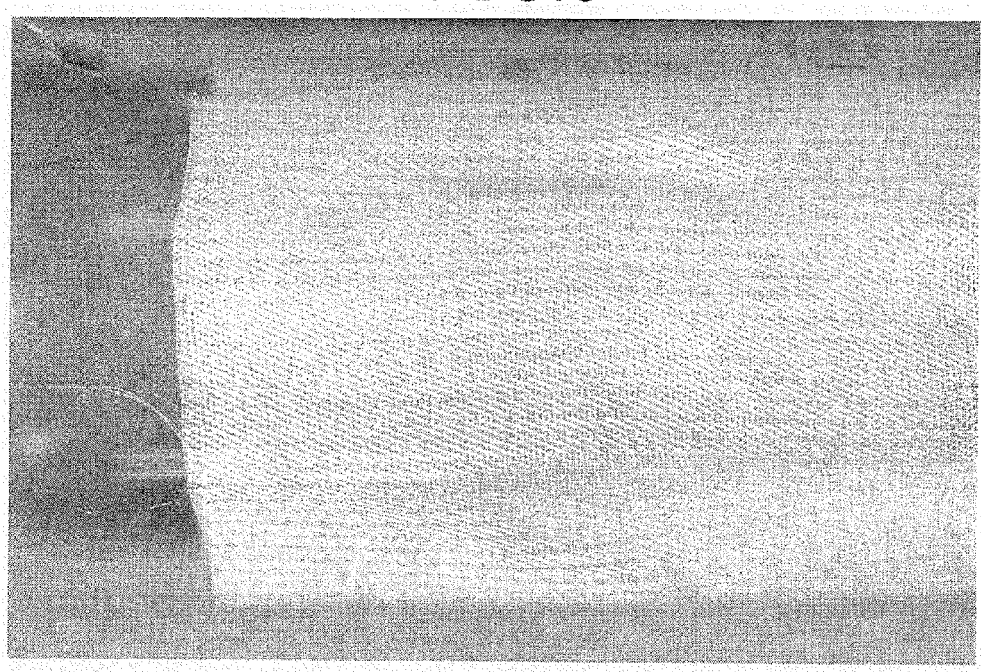
FIG. 5 is a photograph in lieu of drawing showing the fabric according to the present invention after having inserted the stent graft fabric according to the present invention having an outer diameter of 31.2 mm into a sheath, autoclaved the fabric, inserted into a glass tube having an inner diameter of 27.8 mm and expanded (diameter). Deep creases are not observed in the fabric, and the fabric is adhered to the wall of the glass tube as a result of being pushed against it and following its shape.

A metal Z stent was attached to the inside of the fabric A-2 after autoclaving the "sheath-inserted fabric A-2", and then inserted into a glass tube having an inner diameter of 27.8 mm. The measured outer diameter of the fabric A-2 was 31.8 mm. Although this test is inherently to be carried out within a blood vessel, the fabric was inserted into a glass tube for the purpose of visualization. The result is shown in FIG. 5. As a result of observing with the naked eye, there were no deep creases observed in the fabric and the fabric was adhered to the inner wall of the glass tube while following the shape thereof.

Comparative Example 10

Figure 6:
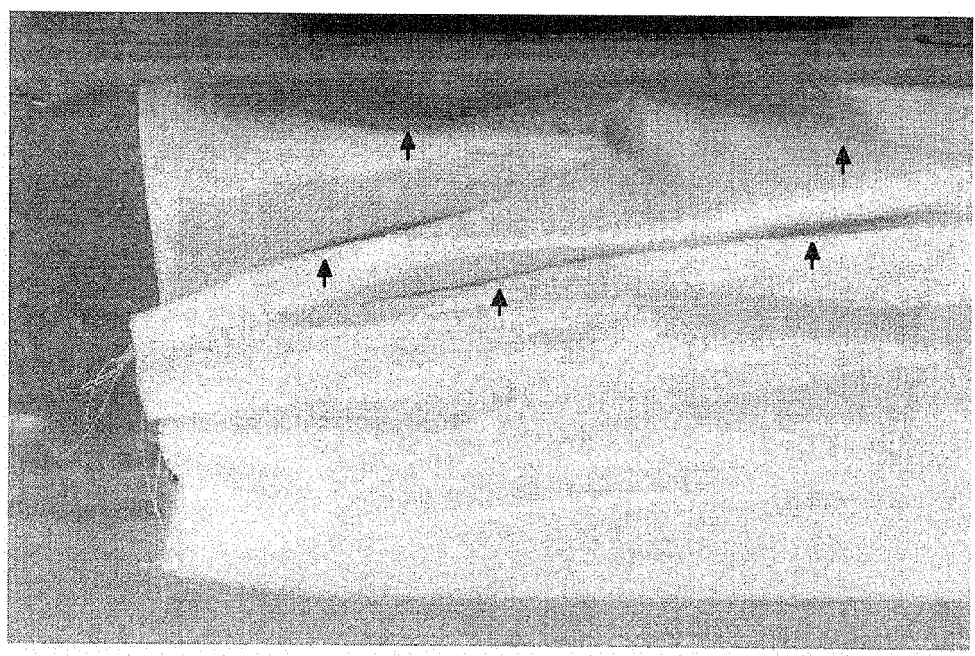
FIG. 6 is a photograph in lieu of drawing showing a commercially available stent graft fabric of the prior art after having inserted the commercially available stent graft fabric of the prior art having an outer diameter of 31.8 mm into a sheath, autoclaved the fabric, inserted into a glass tube having an inner diameter of 27.8 mm and expanded (in diameter). Deep creases (arrows) are observed in the fabric, and even though the fabric is pushed with an expandable member, deep creases open onto the glass tube wall and extend in the form of grooves in the direction of the long axis. If the glass tube were a blood vessel, it is presumed that blood would leak along the grooves of the deep creases.

A metal Z stent was attached to the inside of the fabric D-1 after autoclaving the "sheath-inserted fabric D-1", and then inserted into a glass tube having an inner diameter of 27.8 mm. The measured outer diameter of the fabric D-1 was 31.2 mm. Although this test is inherently to be carried out within a blood vessel, the fabric was inserted into a glass tube for the purpose of visualization. The result is shown in FIG. 6. As a result of observing with the naked eye, creases were clearly observed in the fabric D-1. Although the fabric D-1 was adhered to the glass tube wall as a result of being pushed against it, creases were present despite being compressed by the metal portion of the stent, and the creased portions were lifted from the glass wall. Namely, if the glass tube were a blood vessel, it is presumed that blood would leak from the raised portions and ultimately cause endoleakage phenomenon.

Example 5

Tubes having an inner diameter of 10 mm were produced with the fabric A-2 and the fabric C-1, and the tubes were inserted into Z stents having matching sizes. The stents were fixed within 1 cm from the end of the fabric. An experiment was conducted by implanting the stent grafts into animals. The stent grafts were inserted into the descending thoracic aorta of beagle dogs using sheaths using an aseptic procedure while the dogs were under general anesthesia. The animals remained healthy and were free of health problems during the observation period following surgery. When the vessels were cut open and observed 4 weeks later, each of the fabrics was found to have integrated with the animal vessel walls and become fixed, and although the fabric was attempted to be pulled apart with forceps, it was unable to be separated. There were no creases observed in the fabric. The fabric was then sampled together with the animal vessel to which it had adhered, tissue sections were prepared, and when cross-sections of the sections were observed, countless fibroblasts were observed to have infiltrated between the fiber and vessel wall, collagen fibers were produced around the periphery, and cellular fibrous tissue had formed. Detailed observation of this tissue revealed that long polyester fibers having a cross-sectional diameter of about 3 μm were dispersed within the tissue. The gaps among fiber filaments were large, numerous cells had infiltrated therein, capillaries were observed in some locations, the microfibers and fibroblasts were intermingled and had formed an integrated structure, and the entire fabric was adhered by the cellular fibrous tissue. On the basis of these results, use of the fabric of the present invention is expected to enable the fabric to be reliably fixed to a vessel wall in a landing zone, thereby making it difficult for the graft to migrate.

Comparative Example 11

A tube having an inner diameter of 10 mm was produced with the fabric A-1, the tube was inserted into a Z stent having a matching size, and the stent was then inserted into the descending thoracic aorta of a beagle dog in the same manner as Example 5 followed by observing at 4 weeks after surgery. When the vessel was carefully opened to examine the relationship between the fabric and the animal vessel wall, the fabric A-1 immediately peeled from the vessel wall, and when one end of the fabric was grabbed with forceps, the entire fabric appeared to easily pull apart from the vessel wall. However, there were no thrombi observed between the fabric and the vessel wall. As a result, although there were no creases formed in the fabric and the fabric was tightly pressed against the vessel wall, the fabric and vessel wall were determined not to be integrated. The fabric was then sampled together with the animal vessel, tissue sections were prepared, and when cross-sections thereof were observed, gaps were observed to be present between the fabric and the vessel wall, while infiltration of fibroblasts into the gaps among the filaments of the fabric and production of collagen fibers were not observed. On the basis of these observation results, although the fabric A-1 used microfibers, since the microfibers were closely packed, cells were unable to infiltrate into gaps among the fiber filaments, and integrated adhesion with body tissue was determined to be unable to occur in the landing zone. This phenomenon is presumed to have the risk of leading to graft migration.

Comparative Example 12

A tube having an inner diameter of 10 mm was produced with the fabric D-1 used in Comparative Example 8, the tube was inserted into a Z stent having a matching size, and the stent was then inserted into the descending thoracic aorta of a beagle dog followed by observing at 4 weeks after surgery. When the vessel was carefully opened in the same manner as Comparative Example 11 to examine the relationship between the fabric and the animal vessel wall, the fabric peeled easily. Creases were observed in a portion of the fabric and spaces between the creases and vessel wall were filled with thrombi. When one end of the fabric was grabbed with forceps, the thrombi immediately peeled off after which the entire fabric appeared to easily pull apart from the vessel wall. On the basis of this result, the presence of the creases were determined to have attracted the thrombi, and in addition to suggesting the possibility of inducting endoleakage, the fabric and vessel wall were determined to not be integrated into a single structure. The fabric was then sampled together with the animal vessel, tissue sections were prepared, and when cross-sections thereof were observed, gaps were observed to be present between the fabric and the vessel wall, while infiltration of fibroblasts into the gaps among the filaments of the fabric and production of collagen fibers were not observed. On the basis of these observation results, the fabric D-1 used in Comparative Example 8 was determined to not allowing the obtaining of integrated adhesion with body tissue in the landing zone. This phenomenon is presumed to have the risk of leading to graft migration.

Example 6

A 12 cm portion of a tube of the fabric A-2 was removed and combined with a fabric using a series of three Z stents having a length of 4 cm as an expandable member to produce a stent graft. One centimeter portions on both ends of the fabric were sutured to the metal of the Z stents serving as stent expandable members. Although this site corresponds to a landing zone, due to the presence of microfibers, the fabric had flexibility, excessive force was not applied to the sutures of the metal, and suturing and plication were extremely favorable. Next, the stent graft produced in this manner was inserted into a glass tube having an inner diameter of 27.8 mm using a sheath to simulate an aneurysm, and the stent graft was expanded within the glass tube and positioned therein. This portion was tightly pressed against the glass tube wall and was in a stable state.

Example 7

Figure 7:
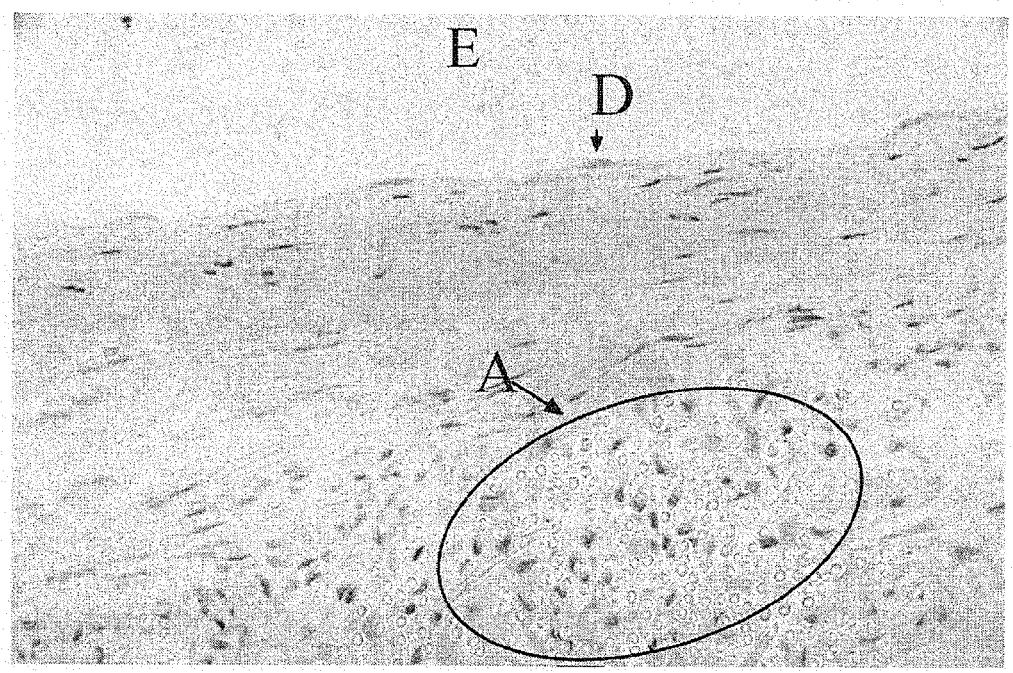
FIG. 7 is a tissue image observed with a light microscope at a magnification of 400× obtained by fabricating a tube having an inner diameter of 10 mm from a fabric (A-2) produced in Example 1, inserting into the descending thoracic aorta of a beagle dog, sampling the tissue six months after surgery and preparing a hematoxylin-stained tissue section thereof (see Example 7).

A tube having an inner diameter of 10 mm was produced with the fabric A-2, and the tube was inserted into the descending thoracic aorta of a beagle dog in the same manner as Example 5 followed by observing six months after surgery. Thrombi were not adhered to the inside of the fabric, and the fabric had a white color that was tinted with a slight pink color. The fabric was adhered to the vessel wall and was unable to be separated even if pulled with forceps. A portion of the tissue was sampled, the tissue sample was fixed in 10% formalin, the fixed tissue was embedded in Technovit resin, sections were prepared using a glass knife to a thickness of 3 μm, and the sections were stained with hematoxylin-eosin stain followed by observing with a light microscope at a magnification of 400×. The results are shown in FIG. 7. Microfiber filaments can be seen to be present in a dispersed state in the lower right portion of the photograph (portion A located within the oval). Individual fiber filaments were dispersed, numerous cells had infiltrated into gaps among the fiber filaments, and tissue had formed in which cells and fiber filaments had integrated into a single structure. Furthermore, the porosity of this portion containing microfibers was 92%. The space (E) shown in the top of the photograph indicates the vessel lumen. A row of cells (D) are arranged along the portion facing the lumen. These are vascular endothelial cells that cover normal vessel inner walls. Thrombi are permanently prevented from adhering to tissue surrounding microfibers covered by vascular endothelial cells, and the microfibers have the same properties as naturally-occurring vessel walls. The presence of microfibers has the characteristic of forming stable tissue. As a result, the dispersed microfiber filaments were demonstrated to have favorable affinity with cells and maintain a favorable relationship over a long period of time.

Comparative Example 13

Figure 8:
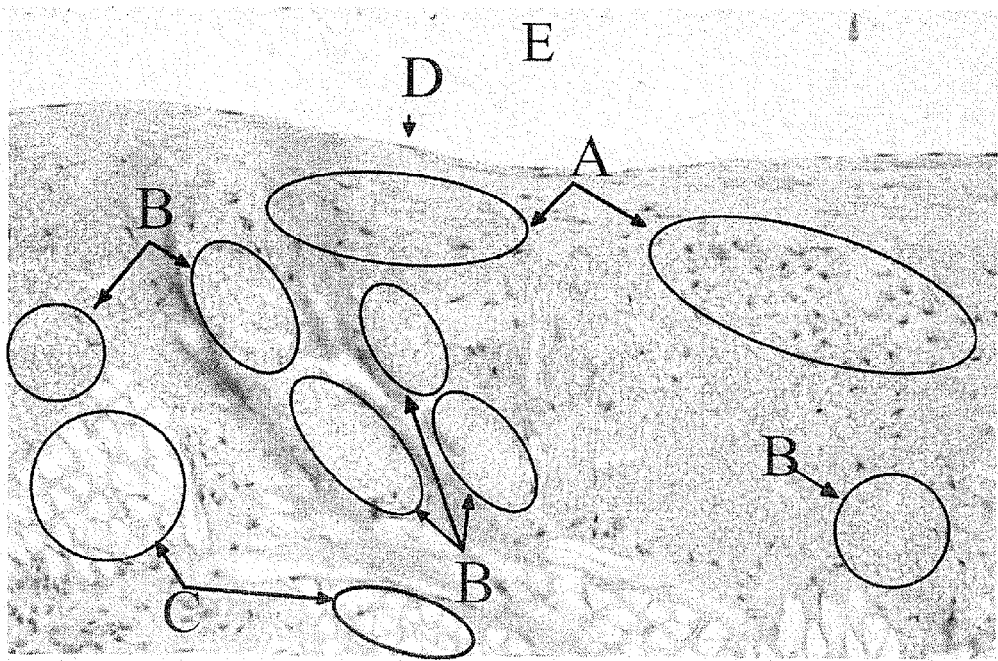
FIG. 8 is a tissue image observed with a light microscope at a magnification of 200× obtained by fabricating a tube having an inner diameter of 10 mm from a fabric (B-2) produced in Comparative Example 3, inserting into the descending thoracic aorta of a beagle dog, sampling the tissue six months after surgery and preparing a hematoxylin-stained tissue section thereof (see Comparative Example 13).

A tube having an inner diameter of 10 mm was produced with the fabric B-2, and the tube was inserted into the descending thoracic aorta of a beagle dog in the same manner as Example 7 followed by observing six months after surgery. Thrombi were not adhered to the inside of the fabric, and the fabric had a white color that was tinted with a slight pink color. The fabric was adhered to the vessel wall and was unable to be separated even if pulled with forceps. A portion of the tissue was sampled, the tissue sample was fixed in 10% formalin, the fixed tissue was embedded in Technovit resin, sections were prepared using a glass knife to a thickness of 3 and the sections were stained with hematoxylin-eosin stain followed by observing with a light microscope at a magnification of 200×. The results are shown in FIG. 8. Thick microfiber filaments can be seen near the bottom of the photograph. These consist of polyester fibers of ordinary thickness. There can be seen to be few cells present among these fibers of ordinary thickness, namely regular fibers (portions indicated with arrows (C) located within ovals). Microfiber filaments can be seen in the form of bundles above the regular fibers, namely in the center of the photograph. This fabric uses thick microfiber bundles and was subjected to water jet treatment at a hydraulic pressure of 70 atm. Thus, microfibers in the upper right portion are in a dispersed state, and the porosity in this portion was about 88%. Numerous cells had infiltrated into the gaps among fiber filaments of the microfiber bundles in the portion having high porosity, and tissue was formed in which cells and fibers had formed an integrated structure. However, microfiber filaments were not dispersed in the central portion of this photograph corresponding to the center of the microfiber bundles. The porosity of this portion was about 28%. Few cells were determined to have infiltrated into the gaps among fiber filaments of the microfibers present in this region of low porosity (portions indicated with arrows B located in ovals). Even though six months had elapsed since the fabric had been implanted in the body, cells had not been incorporated in the gaps among the fiber filaments. In addition, cells had not infiltrated into the gaps among fiber filaments of the regular fibers. Although such a state can be accepted by the body since the polyester fibers consist of an artificial material that does not exhibit cytotoxicity, they cannot be considered to provide a satisfactory environment for cells. Conversely, if microfiber filaments are in a dispersed state in the manner of the previously described Example 7, they can be seen to create a favorable environment for cell infiltration. The space (E) shown in the top of the photograph indicates the vessel lumen. A row of cells (D) are arranged along the portion facing the lumen. As a result, it was determined that it is important for fiber filaments of microfiber bundles to be in a dispersed state, and that the fiber and body tissue become integrated and remain stable over a long period of time when this prescribed dispersed state is formed in a landing zone.

Comparative Example 14

A plain woven tubular fabric having an inner diameter of 32 mm was produced by using regular fiber bundles having a total linear density of 34 dtex/24 filaments for the warp, and combining microfiber bundles having a total linear density of 52 dtex/350 filaments and regular fiber bundles having a total linear density of 34 dtex/24 filaments into a single fiber bundle for use as the weft. This fabric was designated fabric E-1. When the fabric was embedded in Technovit resin and cut into 3 μm sections with a glass knife, and the microfiber portions were photographed with a light microscope at a magnification of 400× followed by calculating porosity from the ratio of the areas of the fiber bundles and the gaps among the fiber filaments using NIH Image software, porosity was found to be 24%. Water jet treatment was then carried out on the fabric E-1 at a hydraulic pressure equivalent to 70 atm. The resulting fabric was designated fabric E-2. When the fabric E-2 was embedded in resin and sections were prepared followed by similarly observing the weft fiber bundles in a cross-section thereof, the porosity was an average of 29%. Thus, it was determined that there are limitations on the degree to which water jet treatment, which is typically used as means to increase porosity, is able to improve porosity as long as a fabric is used in which regular fibers and microfibers are combined for use as the weft. Next, this fabric E-2 was then tested for the "basic requirements" placed on the fabric by the invention of the present application. Since the fabric E-2 had a diameter of 32 mm, it must be able to pass through a hole having a diameter of 3.0 mm. Although the fabric E-2 passes through this hole, there were well-defined creases formed in the fabric after passage as a result of observing with the naked eye.

Comparative Example 15

Microfiber bundles having total linear density of 40 dtex/280 filaments were combined with regular fibers having a total linear density of 17 dtex/12 filaments to form a single fiber bundle. False twist treatment at 4000 twists per meter was then attempted using this fiber bundle. Various conditions thought to be optimum during texturing, including thread tension, twisting speed, temperature and humidity, were selected empirically. Although twisting speed was increased gradually without being excessive, in the case of carrying out false twisting using this procedure, a large number of ruptures were observed in the microfibers. The mechanical load of false twist treatment was presumed to have concentrated in the microfibers due to the effect of the additional presence of the regular fibers, and this was determined to make false twist treatment difficult.

Comparative Example 16

In the present invention, false twist treatment is carried out using microfiber bundles spun by direct spinning. Other examples of methods used to produce the microfibers include island-in-sea and split types, and these methods are characterized by forming a fabric with thick fibers comparable to regular fibers followed by expressing the fibers as microfibers by solvent extraction or heating treatment carried out in a post-processing step. Thus, false twist treatment is presumed to be able to be carried out easily by twisting these fibers while still in the state of thick fibers of the island-in-sea type or split type. Therefore, false twisting was carried out using fibers having an island-in-sea structure, considered to be the most typical among these fibers. As a result, it was not possible to impart at least one or more microcrimps per millimeter. In the case of the island-in-sea type, it was determined that fine false twists are unable to be imparted making it difficult to impart microcrimps as expected since twisting is carried out while still containing styrene and polyester copolymers.

All of the previously described prior art documents and Patent Documents 1 to 10 are incorporated by reference in their entirety in the specification of the present application.

INDUSTRIAL APPLICABILITY

As a result of having superior prevention of endoleakage due to being resistant to creasing and superior prevention of graft migration due to the use of microfibers having superior cytophilicity, the stent graft according to the present invention can be preferably used as a stent graft.

The invention claimed is:

1. A stent graft comprising:
a tubular stent having a central end and a peripheral end, and
a stent graft plain weave fabric covered on said tubular stent,
wherein said stent graft plain weave fabric comprises microfiber bundles as a warp and/or weft,
wherein each of said microfiber bundles consists essentially of 120 to 3000 microfilaments having a filament linear density of 0.5 dtex or less, and each of said microfiber bundles have a total linear density of 10 to 60 dtex, a porosity of 30% to 95% and 10 microcrimp bending points or more per centimeter,
wherein said stent graft plain weave fabric is located in at least 1 cm range from the central end of the tubular stent, and
wherein the weft or the warp is aligned with a longitudinal axis of the tubular stent.

2. The stent graft according to claim 1, wherein each of said microfiber bundles consists essentially of 120 to 2000 microfilaments, and the total linear density of each of the microfiber bundles is 20 to 60 dtex.

3. The stent graft according to claim 1, wherein each of said microfiber bundles consists essentially of 350 to 1500 microfilaments, and the total linear density of each of the microfiber bundles is 20 to 60 dtex.

4. The stent graft according to claim 1, wherein said stent graft plain weave fabric has a thickness of 20 to 90 μm.

5. The stent graft according to claim 1, wherein said stent graft plain weave fabric has a burst strength of 10 to 30 Kg as measured in accordance with a burst strength test in compliance with ANSI/AAMI standards.

6. The stent graft according to claim 1, wherein said stent graft plain weave fabric has a flex-rigidity of 10 to 40 as measured according to the cantilever bending method.

7. The stent graft according to claim 1, wherein said stent graft plain weave fabric has a water permeability of 50 to 1000 ml as measured in accordance with a water permeability test in compliance with ANSI/AAMI standards.

8. The stent graft according to claim 1, wherein the microfilaments are composed of a material selected from the group consisting of polyester, polyamide, polyolefin and polytetrafluoroethylene.

* * * * *

UNITED STATES PATENT AND TRADEMARK OFFICE
CERTIFICATE OF CORRECTION

PATENT NO. : 9,243,353 B2  
APPLICATION NO. : 13/357150  
DATED : January 26, 2016  
INVENTOR(S) : J. Shirokaze et al.

Page 1 of 1

It is certified that error appears in the above-identified patent and that said Letters Patent is hereby corrected as shown below:

In the Claims

At column 25, line 23, please change "have" to -- has --.

Signed and Sealed this
Twenty-fourth Day of May, 2016

Michelle K. Lee
*Director of the United States Patent and Trademark Office*